US012590073B2

(12) United States Patent
Pullagurla et al.

(10) Patent No.: US 12,590,073 B2
(45) Date of Patent: Mar. 31, 2026

(54) PROCESS FOR THE PREPARATION OF MACROCYCLIC CHELANT 2,2',2"-(10-(2-HYDROXYPROPYL)-1,4,7,10-TETRA AZACYCLODODECANE-1,4,7-TRIYL) TRIACETIC ACID AND IT'S COMPLEXES WITH PARAMAGNETIC METAL IONS

(71) Applicant: BIOPHORE INDIA PHARMACEUTICALS PVT. LTD, Hyderabad (IN)

(72) Inventors: Manik Reddy Pullagurla, Hyderabad (IN); Jagadeesh Babu Rangisetty, Hyderabad (IN)

(73) Assignee: BIOPHORE INDIA PHARMACEUTICALS PVT. LTD., Hyderabad (IN)

( * ) Notice: Subject to any disclaimer, the term of this patent is extended or adjusted under 35 U.S.C. 154(b) by 963 days.

(21) Appl. No.: 17/288,146

(22) PCT Filed: Oct. 23, 2019

(86) PCT No.: PCT/IB2019/059044
§ 371 (c)(1),
(2) Date: Apr. 23, 2021

(87) PCT Pub. No.: WO2020/084504
PCT Pub. Date: Apr. 30, 2020

(65) Prior Publication Data

US 2021/0380542 A1 Dec. 9, 2021

(30) Foreign Application Priority Data

Oct. 24, 2018 (IN) ............................ 201841040170

(51) Int. Cl.
*C07D 257/02* (2006.01)

(52) U.S. Cl.
CPC ........ *C07D 257/02* (2013.01); *C07B 2200/13* (2013.01)

(58) Field of Classification Search
CPC .................................................... C07D 257/02
(Continued)

(56) References Cited

U.S. PATENT DOCUMENTS 4,885,363 A 12/1989 Tweedle et al.
5,410,043 A 4/1995 Platzek et al.
(Continued)

FOREIGN PATENT DOCUMENTS

CN 108084105 A 5/2018
EP 3519394 4/2018
(Continued)

OTHER PUBLICATIONS

Reichert et al. Inorganic Chemistry (1996), 35(24), 7013-7020.*
(Continued)

*Primary Examiner* — Kahsay Habte
(74) *Attorney, Agent, or Firm* — McCormick, Paulding & Huber PLLC

(57) ABSTRACT

The present invention relates to an improved process for the preparation of macrocyclic chelant 2,2',2"-(10-(2-hydroxypropyl)-1,4,7,10-tetraazacyclododecane-1,4,7-triyl) triacetic acid of formula (1). The present invention further relates to the process for the preparation of metal complexes of macrocyclic chelant 2,2',2"-(10-(2-hydroxypropyl)-1,4,7,10-tetraazacyclododecane-1,4,7-triyl) triacetic acid of formula (1) with purity greater than 99.0% by HPLC. The present invention also relates to an improved process for the preparation of gadolinium complex of formula (1a) with macrocyclic chelant 2,2',2"-(10-(2-hydroxypropyl)-1,4,7,10-tetraazacyclododecane-1,4,7-triyl) triacetic acid of formula (1). The present invention further relates to a novel process for the preparation of calcium complex of formula (1b) with macrocyclic chelant 2,2',2"-(10-(2-hydroxypropyl)-1,4,7,10-tetraazacyclododecane-1,4,7-triyl) triacetic acid of formula (1).

(1)

(1a)

(Continued)

-continued (1b)

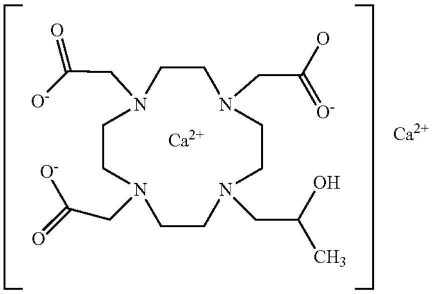

9 Claims, 1 Drawing Sheet

(58) Field of Classification Search
USPC .......................................................... 540/474
See application file for complete search history.

(56) References Cited

U.S. PATENT DOCUMENTS

| | | | | |
|---|---|---|---|---|
| 5,962,679 A | | 10/1999 | Ripa et al. | |
| 6,042,810 A | * | 3/2000 | Ripa .................... | C07D 257/02 540/465 |
| 7,385,041 B2 | | 6/2008 | Chang et al. | |
| 9,447,053 B2 | | 9/2016 | Platzek et al. | |

FOREIGN PATENT DOCUMENTS

| | | |
|---|---|---|
| WO | 2005003105 A1 | 1/2005 |
| WO | 2015075699 A1 | 5/2015 |
| WO | 2018059914 A1 | 4/2018 |

OTHER PUBLICATIONS

Kumar et al. Inorganic Chemistry (1993), 32(20), 4193-4199.*
D. D. Dischino et al., "Synthesis of nonionic gadolinium chelates useful as contrast agents for magnetic resonance maging: 1,4,7-tris(carboxymethyl)-10-substituted-1,4,7,10-tetraazacyclododecanes and their corresponding gadolinium chelates," Inorganic Chemistry, Mar. 1991, vol. 30 No. 6, 1265-1269.
International Search Report for PCT Serial No. PCT/IB2019/059044 dated Feb. 5, 2020.
Supplemental European Search Report for corresponding EP Application No. 19875123.2.

* cited by examiner

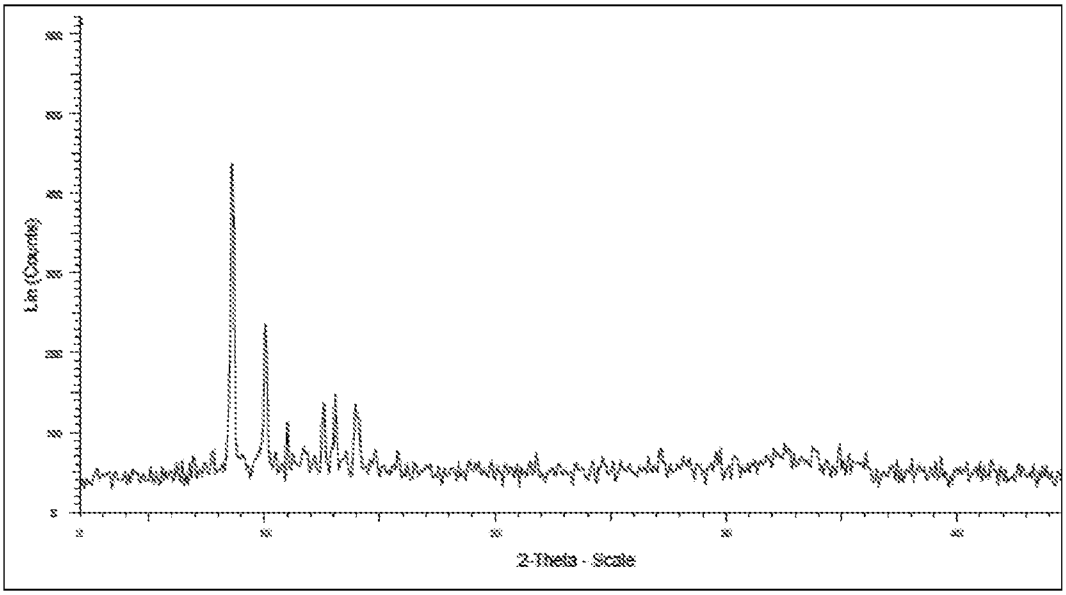
X-Ray powder diffraction (XPRD) pattern of Gadoteridol of formula (1a)

PROCESS FOR THE PREPARATION OF MACROCYCLIC CHELANT 2,2',2"-(10-(2-HYDROXYPROPYL)-1,4,7,10-TETRA AZACYCLODODECANE-1,4,7-TRIYL) TRIACETIC ACID AND IT'S COMPLEXES WITH PARAMAGNETIC METAL IONS

CROSS REFERENCE TO RELATED APPLICATIONS

This application is a National Stage application of International Patent Application No. PCT/IB2019/059044, filed on Oct. 23, 2019, which claims the priority from Indian Patent Application number 201841040170, filed on Oct. 24, 2018, each of which is incorporated by reference in its entirety.

TECHNICAL FIELD

The present invention relates to a novel process for the preparation of macrocyclic chelant 2,2',2"-(10-(2-hydroxypropyl)-1,4,7,10-tetraazacyclododecane-1,4,7-triyl) triacetic acid of formula (1) with purity greater than 99.0%. The present invention also relates to an improved process for the preparation of gadolinium complex of formula (1a) with macrocyclic chelant 2,2',2"-(10-(2-hydroxypropyl)-1,4,7,10-tetraazacyclododecane-1,4,7-triyl) triacetic acid of formula (1) and a novel process for the preparation of calcium complex of formula (1b) with macrocyclic chelant 2,2',2"-(10-(2-hydroxypropyl)-1,4,7,10-tetraazacyclododecane-1,4,7-triyl) triacetic acid of formula (1).

BACKGROUND

Polyamino carboxylic chelants bound with paramagnetic metal ions are useful as a contrast agent in diagnostic medicine. These metal chelating ligands can enhance the resolution of X-ray imaging, radionuclide imaging, ultrasound imaging and magnetic resonance imaging.

Gadoteridol is the gadolinium complex of 10-(2-hydroxypropyl)-1,4,7,10-tetra azacyclododecane-1,4,7-triacetic acid developed by Bracco Diagnostics sold under the brand name ProHance. ProHance (Gadoteridol) injection is a paramagnetic, non-ionic contrast medium for magnetic resonance imaging (MRI).

Calteridol calcium is the calcium complex of 10-(2-hydroxy-propyl)-1,4,7,10-tetra azacyclododecane-1,4,7-triacetic acid used as an excipient to enhance the safety in magnetic resonance imaging (MRI) by diminishing the toxicity of paramagnetic chelate formulations caused by free metal ions and/or free ligands.

The synthesis of Gadoteridol of formula (1a) and Calteridol calcium of formula (1b) was reported in many patents and non-patent literature. The contents of which are hereby incorporated as reference in their entirety.

U.S. Pat. No. 4,885,363 patent disclosed the process for the preparation of Gadoteridol of formula (1a) by reacting 1,4,7,10-tetraazacyclododecane disulfate (II) of formula (7) with excess of chloroacetic acid of formula (8) in presence of potassium hydroxide to obtain 1,4,7-Triscarboxymethyl-1,4,7,10-tetraazacyclo dodecane of formula (9). Compound of formula (9) undergo alkylation with propylene oxide of formula (2) under basic condition yields 1,4,7-triscarboxymethyl-10-(2'-hydroxy propyl)-1,4,7,10-tetraazacyclododecane as ammonium salt of formula (1). Reacting compound of formula (1) with Gadolinium acetate tetrahydrate under basic condition furnished Gadoteridol of formula (1a). The obtained compound was further purified by preparative HPLC and does not disclosed the purity of compound. The above process involves expensive purification process for preparing pure Gadoteridol of formula (1a).

Scheme 1

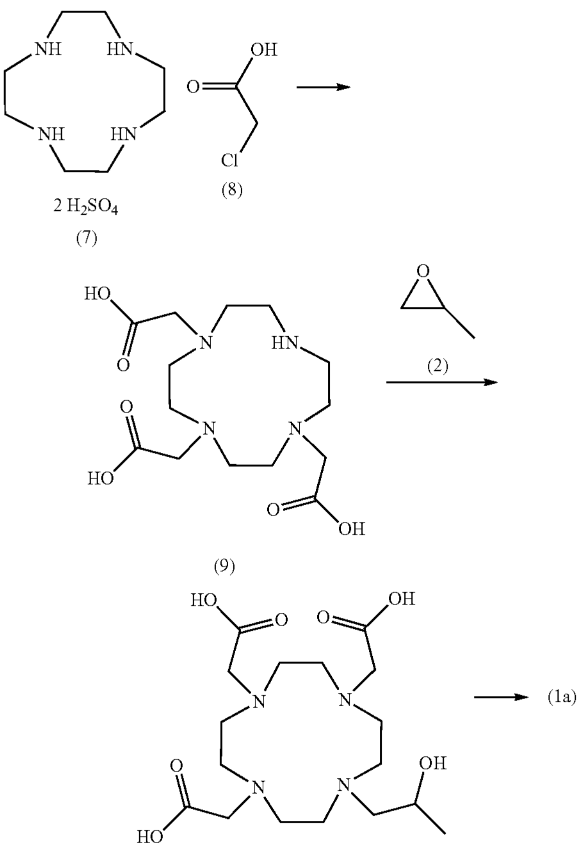

$2\ H_2SO_4$ (7)

(8)

(9)

(1)

(1a)

U.S. Pat. No. 5,410,043 patent disclosed the process for the preparation of Gadoteridol of formula (1a) by reacting cyclen of formula (6) with dimethylformamide-dimethylacetal in toluene to form 1,4,7,10-tetra azatricyclo [5.5.1.0] tridecane of formula (10), azeotroped with mixture of methanol/dimethyl amine/toluene. Alkylation of intermediate of formula (10) with propylene oxide under basic condition in methanol at reflux temperature for 24 h yields intermediate of formula (11), azeotroped with water and methanol mixture. Added sodium hydroxide to the reaction mixture and refluxed for 8 h, finally isolated with n-butanol and ethyl acetate gave intermediate of formula (12). Reacting intermediate of formula (12) with chloroacetic acid under basic medium at 80° C. for 22 h provides compound of formula (1), which was precipitated from a mixture of methanol and ethanol. Compound (1) was purified by ion exchange column by using 10% ammonia solution as eluent. Finally, reacting compound of formula (1) with Gadolinium oxide and glacial acetic acid at 90° C. for 6 h furnished Gadoteridol of formula (1a). The obtained compound was purified several times by ion exchange column cascade under HPLC control and does not disclosed the purity of compound.

Scheme 2

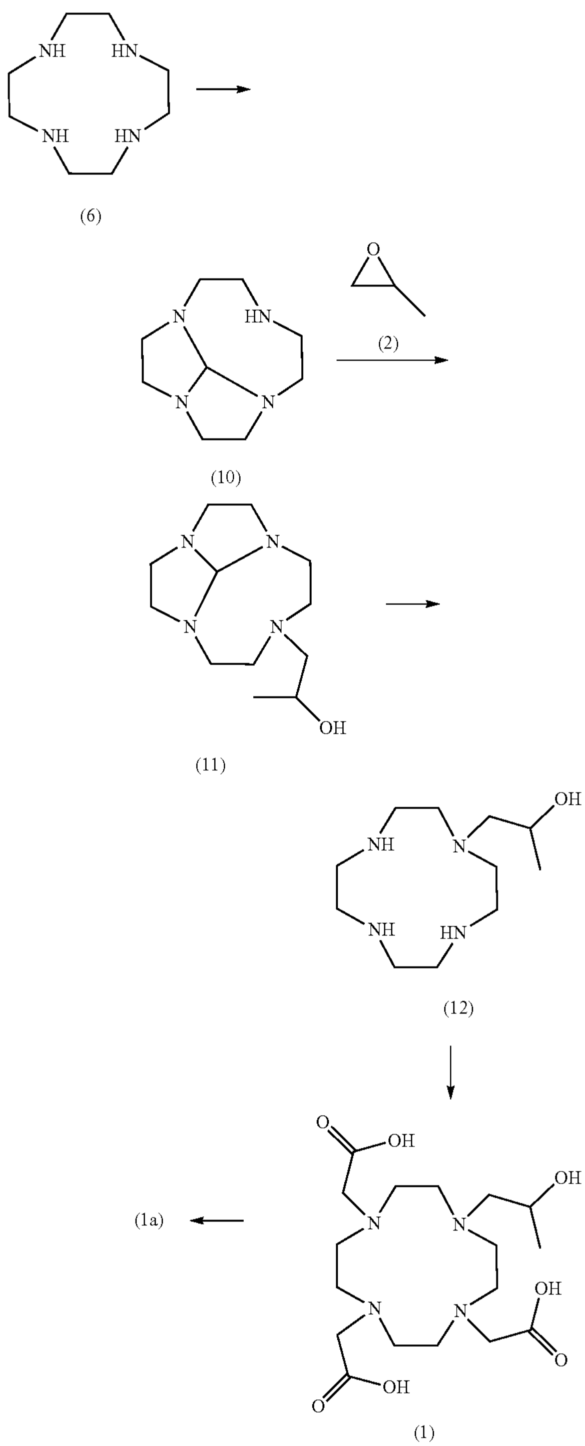

(6)

(10)

(11)

(12)

(1)

(1a)

U.S. Pat. No. 7,385,041 patent disclosed the preparation of Calteridol calcium of formula (1b) by reacting compound of formula (1) with calcium carbonate in water at 90° C. for 2.5 hours. The obtained white solid was recrystallized from water:acetone. The reaction results in producing carbonic acid as a byproduct which makes the solution acidic in nature.

Scheme 3

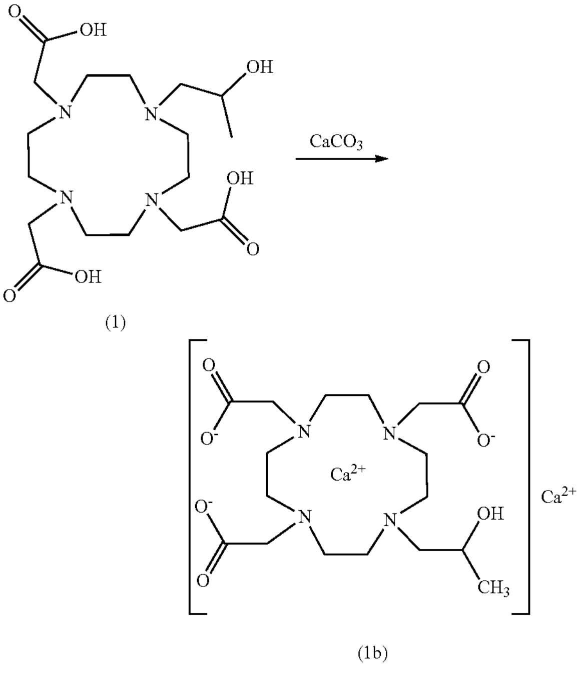

(1)

(1b)

Prior art processes involve synthesis of Gadoteridol of formula (1a) tangled with drawbacks like a greater number of steps, lack of desired purity, long period of reaction time, requires purification in each step and purification of API through preparative HPLC which is expensive and not suitable for industrial scale purposes. Using too many different solvents at each step makes the process tedious and not feasible at commercial level.

To overcome the above discussed process hurdles, the present invention, provides a simple, economical and industrially feasible process for preparation of Gadoteridol of formula (1a) and Calteridol calcium of formula (1b).

OBJECTIVE OF THE INVENTION

The objective of the present invention is to provide a novel process for the preparation of 2,2',2"-(10-(2-hydroxypropyl)-1,4,7,10-tetraaza cyclododecane-1,4,7-triyl) triacetic acid of formula (1).

Another objective of the present invention is to provide process for the preparation of metal complexes of 2,2',2"-(10-(2-hydroxy propyl)-1,4,7,10-tetra azacyclododecane-1,4,7-triyl) triacetic acid of formula (1).

Another objective of the present invention is to provide an improved process for the preparation of Gadoteridol of formula (1a) with purity greater than 98.0% by High performance liquid chromatography (HPLC).

In another objective, Gadoteridol of formula (1a) obtained in the present invention is having X-ray powder diffractogram as depicted in FIG. 1.

Another objective of the present invention is to provide a novel process for the preparation of Calteridol calcium of formula (1b) from chelating ligand 2,2',2"-(10-(2-hydroxypropyl)-1,4,7,10-tetraazacyclododecane-1,4,7-triyl) triacetic acid of formula (1). It further provides a novel process for the preparation of Calteridol calcium of formula (1b) from Gadoteridol of formula (1a).

Another objective of the present invention is to provide pure Calteridol calcium of formula (1b) with purity greater than 99.0% by High performance liquid chromatography (HPLC).

In another objective of the invention, Calteridol calcium of formula (1b) obtained in the present invention is amorphous.

SUMMARY OF THE INVENTION

In one aspect, the present invention provides a process for the preparation of 2,2',2"-(10-(2-hydroxypropyl)-1,4,7,10-tetraaza cyclododecane-1,4,7-triyl) triacetic acid of formula (1) comprising:

a) reacting 1,4,7,10-tetraazacyclododecane of formula (6) with tert-butyl 2-bromoacetate of formula (5) to obtain tert-butyl 2,2',2"-(1,4,7,10-tetraazacyclododecane-1,4,7-triyl) triacetate hydrobromide of formula (4);

b) hydrolysing tert-butyl 2,2',2"-(1,4,7,10-tetraazacyclo dodecane-1,4,7-triyl) triacetate hydrobromide of formula (4) to obtain 2,2',2"-(1,4,7,10-tetraazacyclododecane-1,4,7-triyl) triacetic acid of formula (3), optionally isolating intermediate of formula (3);

c) alkylating 2,2',2"-(1,4,7,10-tetraazacyclododecane-1,4,7-triyl) triacetic acid compound of formula (3) with propylene oxide of formula (2) to yield 2,2',2"-(10-(2-hydroxypropyl)-1,4,7,10-tetraazacyclo dodecane-1,4,7-triyl) triacetic acid of formula (1).

In another aspect, the present invention provides an improved process for the preparation of Gadoteridol of formula (1a) comprising:

d) complexing the chelate ligand 2,2',2"-(10-(2-hydroxypropyl)-1,4,7,10-tetraazacyclododecane-1,4,7-triyl) triacetic acid of formula (1) with Gadolinium oxide to yield Gadoteridol of formula (1a). Optionally, purifying the formula (1a)

Another aspect, the present invention provides simple purification process for Gadoteridol of formula (1a) to obtain with purity greater than 99.0% by High performance liquid chromatography (HPLC), which comprising of:

i. providing a solution of Gadoteridol of formula (1a) in protic solvent or mixture thereof;

ii. treating with suitable acidic resin;

iii. filtering the reaction mass;

iv. treating with suitable basic resin; and

V. isolating pure Gadoteridol of formula (1a).

In another aspect, the present invention provides Gadoteridol of formula (1a) with regio isomer of formula (13) content less than 2% (w/w), more preferably less than 1% (w/w) and still more preferably less than 0.5% (w/w).

In another aspect, the present invention provides Gadoteridol of formula (1a) with related impurities of impurity A less than 0.01% (w/w), impurity B less than 0.1% (w/w) and impurity D less than 0.1% (w/w).

In another aspect, the present invention provides Gadoteridol of formula (1a) with total impurities less than 0.5%, preferably less than 0.2% and more preferably less than 0.1%.

In another aspect, the present invention provides Gadoteridol of formula (1a) having water content less than 14% by Karl Fischer (KF) method, preferably less than 10%.

In another aspect, the present invention provides Gadoteridol of formula (1a) with metal content, lead level less than 2 ppm, Arsenic level less than 3 ppm and Iron level less than 5 ppm.

Still another aspect, Gadoteridol of formula (1a) obtained in the present invention is having X-ray powder diffractogram as depicted in FIG. 1.

In another aspect, the present invention provides a novel process for the preparation of Calteridol calcium of formula (1b) from chelating ligand 2,2',2"-(10-(2-hydroxypropyl)-1,4,7,10-tetraazacyclododecane-1,4,7-triyl) triacetic acid of formula (1) comprising:

a) complexing the chelating ligand 2,2',2"-(10-(2-hydroxypropyl)-1,4,7,10-tetraazacyclododecane-1,4,7-triyl) triacetic acid of formula (1) with calcium ion source to yield Calteridol calcium of formula (1b)

In another aspect, the present invention provides a novel process for the preparation of Calteridol calcium of formula (1b) from Gadoteridol of formula (1a) comprising:

i. de-complexing the Gadolinium complex of 2,2',2"-(10-(2-hydroxypropyl)-1,4,7,10-tetraazacyclododecane-1,4,7-triyl) triacetic acid of formula (1a) with suitable de-complexing agent to provide a solution of compound of formula (1) and precipitating Gadolinium salt; and ii. complexing compound of formula (1) with a calcium ion source to yield Calteridol of formula (1b)

In another aspect, the present invention provides substantially pure Calteridol calcium of formula (1b) with purity greater than 98.0% by High performance liquid chromatography (HPLC).

In another aspect, the present invention provides Calteridol of formula (1b) with total impurities less than 0.5% (w/w), preferably less than 0.3% (w/w).

In another aspect, the present invention provides Calteridol calcium of formula (1b) with Tri acid impurity less than 0.5%, DOTA impurity less than 0.5% (w/w) and Regio isomer impurity (13) less than 1.0% (w/w) and more preferably less than 0.5% (w/w).

In another aspect, the present invention provides Calteridol calcium of formula (1b) with metal content, Lead level less than 2 ppm, Arsenic level less than 3 ppm and Iron level less than 5 ppm.

In another aspect, Calteridol calcium of formula (1b) obtained in the present invention is having calcium content about 10 to 15% (w/w).

Yet another aspect, Calteridol of formula (1b) obtained in the present invention is having amorphous nature.

DETAILED DESCRIPTION OF THE INVENTION

As referred herein, "solvent" used in any reaction step of present invention is selected from following solvent as single solvent or mixture thereof. The suitable protic solvent used in the present invention may be selected from the group comprising of alcoholic solvent $C_{1-6}$ linear or branched alcohol, acids such as methanol, ethanol, isopropanol, propanol, butanol, water, acetic acid or the like. Preferably, water, isopropanol and methanol were used in the present invention.

The suitable aprotic solvent used in the present invention may be selected from the group comprising of chlorinated hydrocarbons such as dichloromethane, dichloroethane, chloroform or carbon tetrachloride; aromatic hydrocarbon such as toluene, xylene, chlorobenzene, bromobenzene; ether such as dioxane, tetrahydrofuran (THF), methyl tert-butyl ether (MTBE), ethylene glycol, dimethyl ether, diethyl ether; nitriles such as acetonitrile; ester such as ethyl acetate, isopropyl acetate; ketone such as acetone, methyl isobutyl ketone (MIBK), methyl ethyl ketone (MEK); polar aprotic such as N,N-dimethylformamide, dimethyl sulfoxide, dimethyl acetamide, N-methylpyrrolidone (NMP) or the like. Preferably, dimethylformamide, acetone and toluene were used in the present invention.

As referred herein, the term "base" used in any reaction step of present invention is selected from following base as single or in any combination or in aqueous form depending upon the kind and nature of the reaction. The suitable base used in the present invention may be selected from the group comprising of inorganic and organic bases. Inorganic base includes alkoxide, hydroxide, carbonate, bicarbonate or hydride of alkali or alkaline earth metal, acetates, phosphates are selected from sodium tertbutoxide, potassium tertbutoxide, lithium methoxide, lithium ethoxide, sodium methoxide, sodium ethoxide, potassium methoxide, potassium ethoxide, sodium hydroxide, potassium hydroxide, lithium hydroxide, cesium hydroxide, potassium carbonate, sodium carbonate, cesium carbonate, lithium carbonate, sodium bicarbonate, potassium bicarbonate, lithium bicarbonate, sodium amide, 20 sodium hydride, potassium hydride, lithium hydride, sodium acetate, potassium acetate, potassium phosphate, sodium phosphate or the like. Organic base includes triethylamine (TEA), diethylamine (DEA), tripropyl amine, quinoline, piperidine, N-Ethyldiisopropyl amine, dimethyl aniline, N-methyl morpholine, 1,8-diazabicyclo[5.4.0]undec-7-ene (DBU), diisopropyl ethylamine (DIPEA) and 1,4-diazabicyclo[2.2.2]octane (DABCO), imidazole, N,N-dimethyl aniline, pyridine, N,N-dimethyl amino pyridine (DMAP), 1,5-diazabicyclo[4.3.0]non-5-ene (DBN), n-butyl lithium, lithium diisopropylamide (LDA), lithium hexamethyldisilazide (LiHMDS), sodium 5 hexamethyldisilazide (NaHMDS), potassium hexamethyldisilazide (KHMDS) or the like. Preferably, sodium acetate and sodium hydroxide were used in the present invention.

As referred herein, the term "resin" used in any reaction step of present invention is selected from following resins. The suitable acidic resin used were selected from a group comprising of Indion 225 Na, Indion 220 Na, Indion 225 H, Indion 225 H (MB), Indion 236, Indion 740, Indion 730, Amberlite IRC 50 or the like. Preferably, Indion 225 $H^+$ acidic resin was used. The suitable basic resin used was selected from a group comprising of Indion 810, Amberlite IRA 67 or the like. Preferably, Indion 810 $^-OH$ basic resin was used in the present invention.

Accordingly, in one embodiment, the present invention provides an improved process for the preparation of 2,2',2"-(10-(2-hydroxypropyl)-1,4,7,10-tetraaza cyclododecane-1,4,7-triyl) triacetic acid of formula (1) as shown in scheme 4 comprising:

a) reacting 1,4,7,10-tetraazacyclododecane of formula (6) with tert-butyl 2-bromoacetate of formula (5) to obtain a compound tert-butyl 2,2',2"-(1,4,7,10-tetraazacyclododecane-1,4,7-triyl) triacetate hydrobromide of formula (4);
b) hydrolysing tert-butyl 2,2',2"-(1,4,7,10-tetraazacyclo dodecane-1,4,7-triyl) triacetate hydrobromide of formula (4) to obtain 2,2',2"-(1,4,7,10-tetraazacyclododecane-1,4,7-triyl) triacetic acid of formula (3), optionally isolating intermediate of formula (3);
c) alkylating 2,2',2"-(1,4,7,10-tetraazacyclododecane-1,4,7-triyl) triacetic acid compound of formula (3) with propylene oxide of formula (2) to yield 2,2',2"-(10-(2-hydroxypropyl)-1,4,7,10-tetraazacyclo dodecane-1,4,7-triyl) triacetic acid of formula (1).

Scheme 4: Synthesis of 2,2',2"-(10-(2-hydroxypropyl)-1,4,7,10-tetraazacyclododecane-1,4,7-triyl) triacetic acid of formula (1)

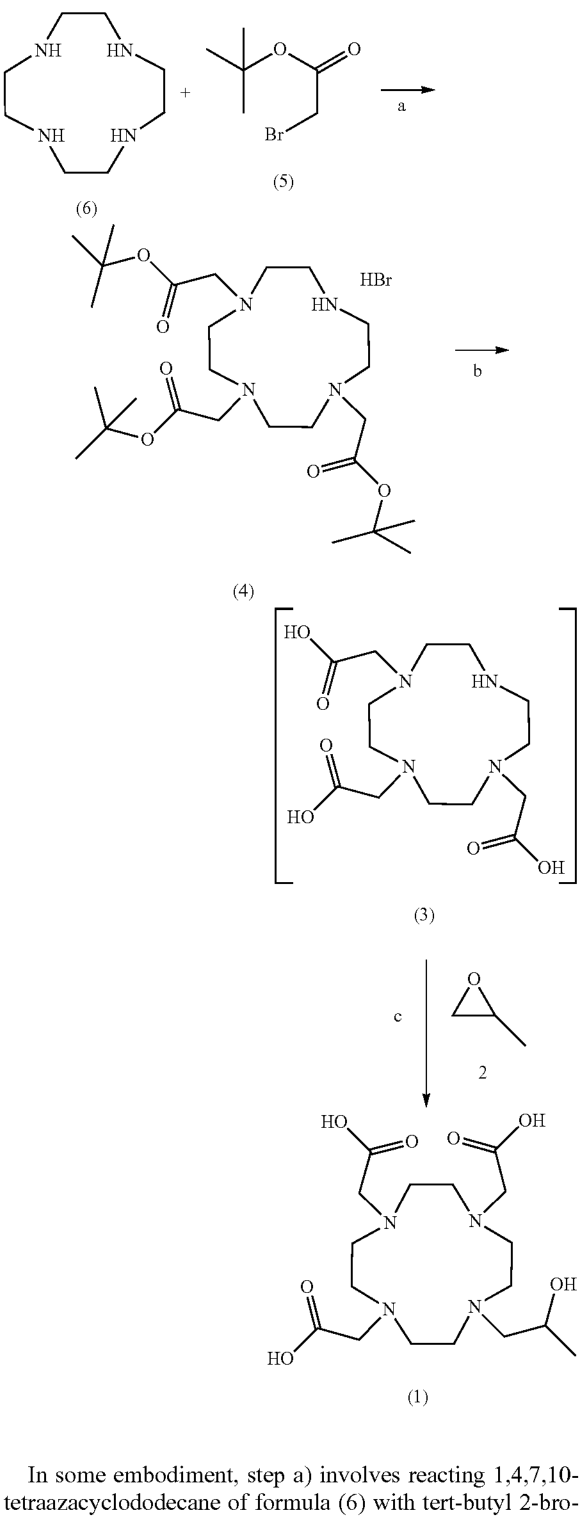

(6) (5) (4) (3) (1)

In some embodiment, step a) involves reacting 1,4,7,10-tetraazacyclododecane of formula (6) with tert-butyl 2-bromoacetate of formula (5) in presence of suitable base in a suitable aprotic solvent to provide a compound tert-butyl 2,2',2"-(1,4,7,10-tetraazacyclododecane-1,4,7-triyl) triacetate hydrobromide of formula (4). The obtained formula (4) may be purified and isolated from a suitable aprotic solvent with a purity greater than 97.0%. None of the prior arts mentioned the purity of intermediate compounds.

Step b) proceeds with hydrolysis of tert-butyl 2,2',2"-(1,4,7,10-tetraazacyclododecane-1,4,7-triyl) triacetate hydrobromide of formula (4) to 2,2',2"-(1,4,7,10-tetraazacyclo dodecane-1,4,7-triyl) triacetic acid of formula (3) in presence of suitable base in a protic solvent. Optionally, isolating the compound 2,2',2"-(1,4,7,10-tetraazacyclo dodecane-1,4,7-triyl) triacetic acid of formula (3).

Step c) proceeds with alkylating compound of formula (3) by reacting with propylene oxide of formula (2) in a protic solvent at to obtain 2,2',2"-(10-(2-hydroxypropyl)-1,4,7,10-tetraazacyclododecane-1,4,7-triyl) triacetic acid of formula (1). Compound of formula (1) so formed was purified by treating with suitable protic and aprotic solvents carried out at a suitable temperature. The present invention controls the formation of regio-isomer impurity of formula (13) to a limit of less than 2% (w/w), more preferably to less than 1% (w/w) and more preferably less than 0.5% (w/w).

In another embodiment, the present invention provides an improved process for the preparation of Gadoteridol of formula (1a) as shown in scheme 5 comprising:

d) complexing 2,2',2"-(10-(2-hydroxypropyl)-1,4,7,10-tetraazacyclododecane-1,4,7-triyl) triacetic acid of formula (1) with Gadolinium oxide to yield Gadoteridol of formula (1a)

Scheme 5: Synthesis of Gadoteridol of formula (1a)

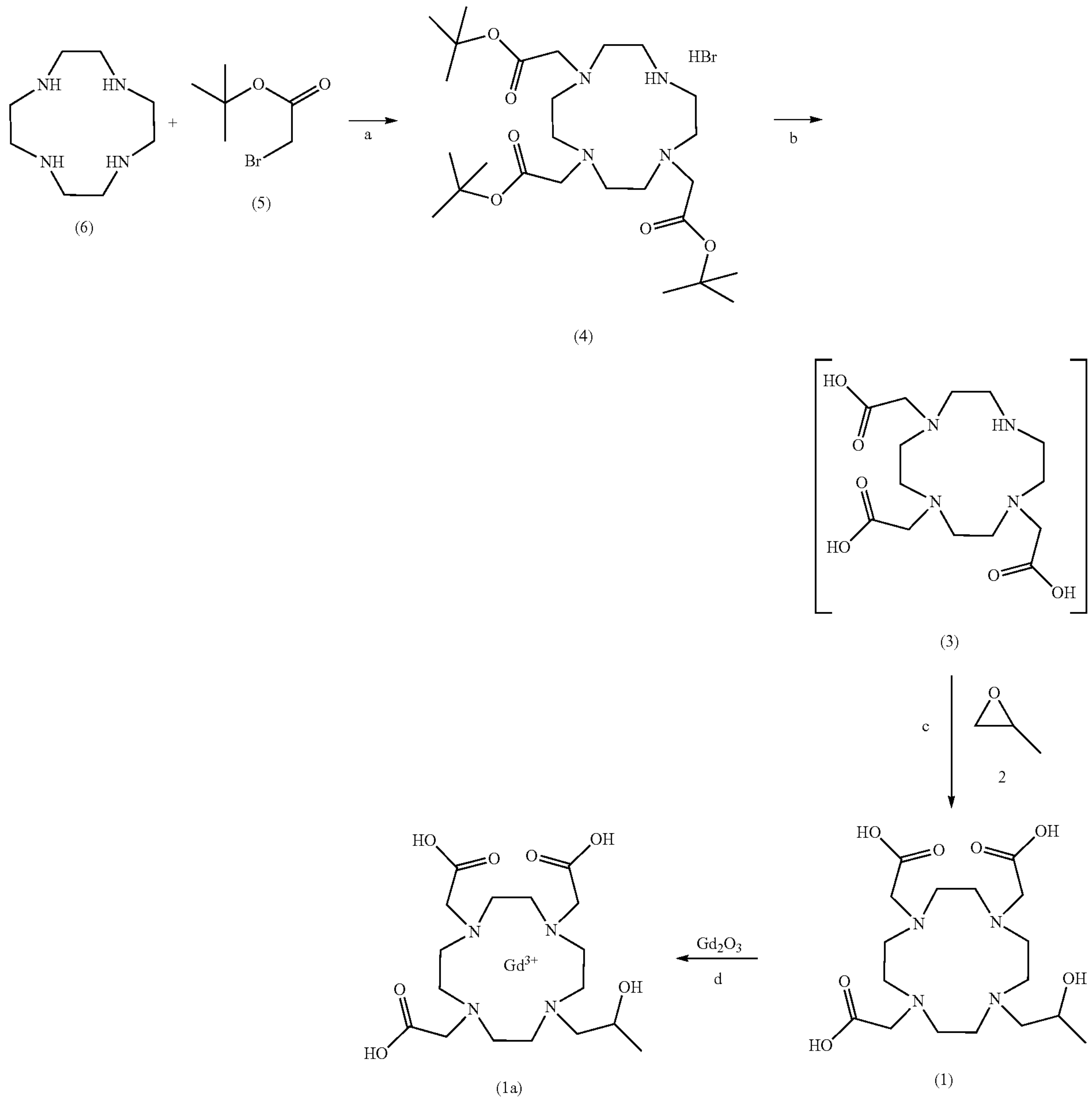

(6)
(5)
(4)
(3)
2
(1)
(1a)

Step d) proceeds with complexation of 2,2',2"-(10-(2-hydroxy propyl)-1,4,7,10-tetraazacyclododecane-1,4,7-triyl) triacetic acid of formula (1) with Gadolinium ion source in protic solvent to provide Gadoteridol of formula (1a). The obtained Gadoteridol of formula (1a) was purified by treating with suitable acidic and basic resin to remove the undesired salts. Optionally, Gadoteridol of formula (1a) was purified and isolated from protic and aprotic solvents.

The Gadolinium ion source used in the step d) of the present invention was selected from the group comprising of Gadolinium hydroxide, Gadolinium oxide, Gadolinium carbonate, Gadolinium chloride, Gadolinium acetate, or the like. Preferably, Gadolinium oxide was used in the present invention.

In another embodiment, the present invention provides a process for purification of Gadoteridol of formula (1a), comprising of:

i. providing a solution of Gadoteridol of formula (1a) in protic solvent or mixture thereof;
ii. treating with suitable acidic resin;
iii. filtering the reaction mass;
iv. treating with suitable basic resin; and
V. isolating pure Gadoteridol of formula (1a).

In some embodiment, purification of Gadoteridol of formula (1a) involves, dissolving in a suitable protic solvent, preferably water, methanol, or mixtures thereof, and adjusting the pH to 3-4 using a suitable acidic resin, preferably 225H+ acidic resin and filtered. To the filtrate 810 OH— resin may be added and pH maintained at 7.0 to 8.0 and filtered. The filtrate may be treated with activated carbon and filtered, preferably through Hyflo and 0.2-micron filter. The filtrate so obtained may be distilled off and crude dissolved in a suitable protic solvent, heated and isolated to yield pure Gadoteridol of formula (1a).

In another embodiment, pure Gadoteridol of formula (1a) obtained after purification is having purity greater than 99.0%, preferably more than 99.5%, more preferably greater than 99.8% by High performance liquid chromatography (HPLC).

In another embodiment, Gadoteridol of formula (1a) obtained after purification is having total impurities less than 1.0% (w/w), more preferably less than 0.5% (w/w).

In another embodiment, Gadoteridol of formula (1a) obtained after purification has Regio isomer impurity of formula (13) content less than 2% (w/w), more preferably less than 1% (w/w).

In another embodiment, Gadoteridol of formula (1a) obtained after purification is having impurity A less than 0.01% (w/w) and impurities B, C, D, E, F are less than 0.1% (w/w).

Impurity A

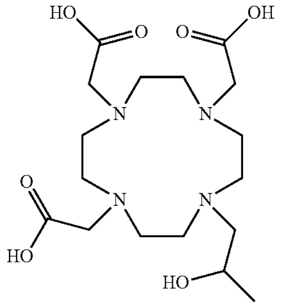

-continued

Impurity B

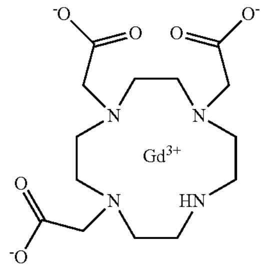

Impurity C

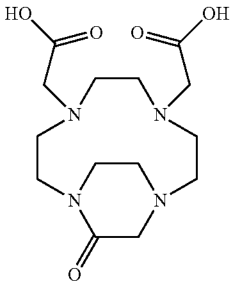

Impurity D

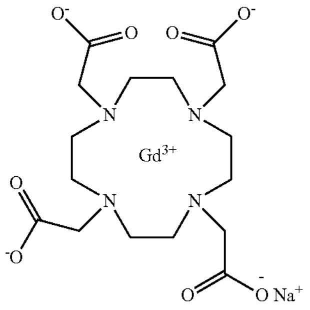

Impurity E

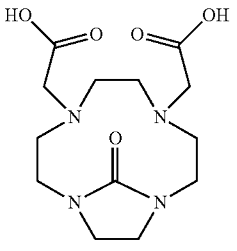

Impurity F

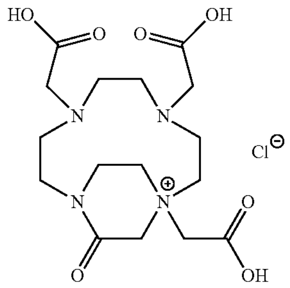

In another embodiment, Gadoteridol of formula (1a) obtained after purification is having content less than 15% (w/w) by Karl Fischer method and it exists as a hydrated form of Gadoteridol of formula (1a).

In another embodiment, the present invention provides Gadoteridol of formula (1a) obtained after purification is having with metal content lead level less than 2 ppm, Arsenic level less than 3 ppm and Iron level less than 5 ppm. In another embodiment, the present invention provides gadoteridol of formula (1a) having free gadolinium content less than 50 ppm and more preferably less than 10 ppm.

Yet, in another embodiment, Gadoteridol of formula (1a) obtained in the present invention is having X-ray powder diffractogram as depicted in FIG. 1, table 1.

TABLE 1

| 2(theta) values | Relative Intensity ($I/I_0$) |
|---|---|
| 3.20 | 11.2 |
| 6.40 | 14.6 |
| 6.96 | 15.8 |
| 7.44 | 13.7 |
| 7.76 | 17.5 |
| 8.62 | 100 |
| 9.04 | 16.3 |
| 10.08 | 53.8 |
| 10.48 | 16.9 |
| 11.03 | 25.6 |
| 11.28 | 16.4 |
| 11.67 | 18.2 |
| 12.09 | 15.9 |
| 12.48 | 31.0 |
| 13.06 | 33.7 |
| 13.44 | 17.1 |
| 13.96 | 31.1 |
| 14.78 | 17.7 |
| 15.84 | 17.2 |
| 16.21 | 13.5 |
| 16.56 | 14.0 |
| 17.55 | 12.7 |
| 18.84 | 14.5 |
| 19.76 | 14.4 |
| 20.13 | 12.8 |
| 20.48 | 13.5 |
| 21.52 | 14.1 |
| 21.84 | 16.6 |
| 22.80 | 13.5 |
| 24.66 | 15.3 |
| 25.47 | 14.3 |
| 26.64 | 15.3 |
| 27.10 | 18.1 |
| 29.73 | 18.1 |
| 30.41 | 15.8 |
| 32.78 | 18.1 |
| 33.93 | 17.8 |
| 34.36 | 14.8 |
| 34.96 | 19.1 |
| 36.07 | 17.2 |
| 37.22 | 13.0 |
| 38.08 | 15.0 |
| 38.36 | 13.4 |
| 40.48 | 14.2 |
| 40.88 | 12.6 |
| 44.72 | 11.7 |

In another embodiment, the present invention provides a novel process for the preparation of Calteridol calcium of formula (1b) from chelating ligand 2,2',2"-(10-(2-hydroxypropyl)-1,4,7,10-tetraazacyclododecane-1,4,7-triyl) triacetic acid of formula (1) as illustrated in scheme 6 comprising:

A. complexing the chelating ligand 2,2',2"-(10-(2-hydroxypropyl)-1,4,7,10-tetraazacyclododecane-1,4,7-triyl) triacetic acid of formula (1) with calcium ion source to yield Calteridol calcium of formula (1b)

Scheme 6: Synthesis of Calteridol calcium of formula (1b)

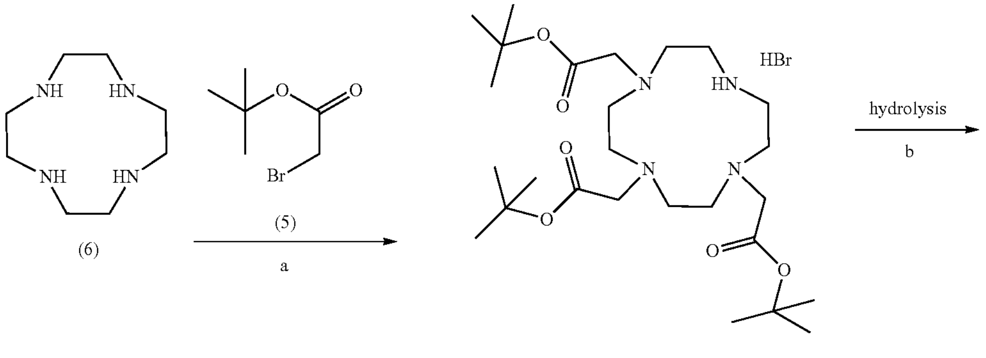

(6) (5) (4)

-continued

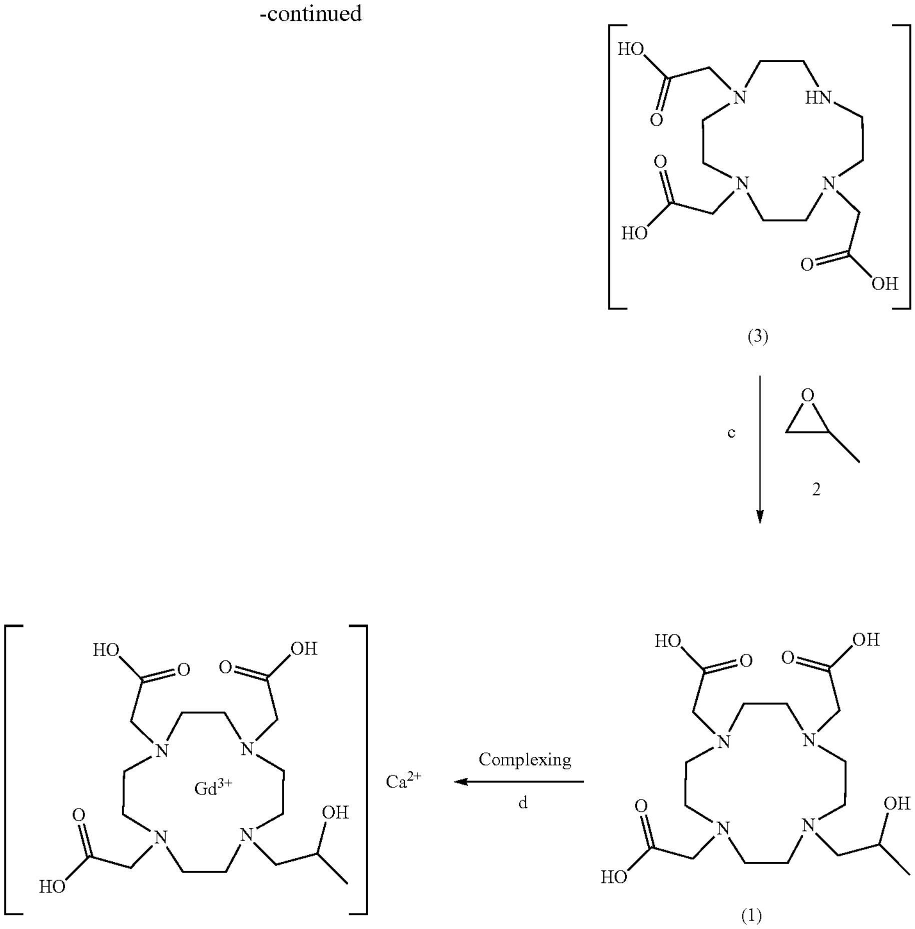

(3)

(1)

(1b)

Step A) proceeds with complexation of 2,2',2"-(10-(2-hydroxy propyl)-1,4,7,10-tetraazacyclododecane-1,4,7-triyl) triacetic acid of formula (1) with calcium ion source in protic solvent to provide Calteridol calcium of formula (1b). Optionally, Calteridol calcium of formula (1b) obtained was purified from protic and aprotic solvents.

The calcium ion source used in the step d) of the present invention was selected from the group comprising of calcium hydroxide, calcium oxide, calcium carbonate calcium chloride, calcium acetate, or the like. Preferably, calcium hydroxide was used in the present invention.

In another embodiment, the present invention provides a novel process for the preparation of Calteridol of formula (1b) from Gadoteridol of formula (1a) as shown in scheme 7 comprising:

i. de-complexing the Gadolinium complex of 2,2',2"-(10-(2-hydroxypropyl)-1,4,7,10-tetraazacyclododecane-1,4,7-triyl) triacetic acid of formula (1a) with suitable de-complexing agent to provide a solution of free chelating ligand and a precipitated Gadolinium salt; and ii. complexing the free chelating ligand with a calcium ion source to obtain Calteridol calcium of formula (1b)

Scheme 7: Synthesis of Calteridol calcium of formula (1b) from Gadoteridol (1a)

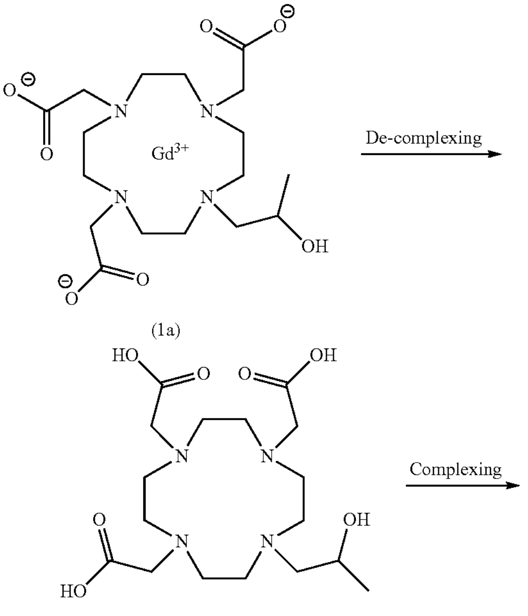

(1a)

(1)

-continued

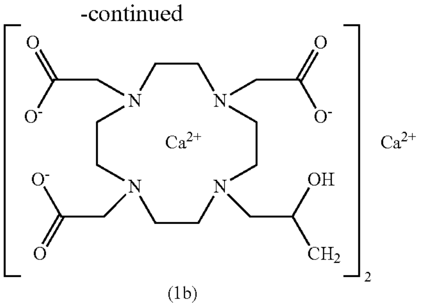

(1b)

Step i) proceeds with de-complexing the Gadoteridol of formula (1a) with a suitable de-complexing agent, preferably using oxalic acid or phosphoric acid to provide a solution of free chelating ligand of formula (1) in a suitable polar solvent. Optionally, compound of formula (1) was purified by treating with suitable resins, isolated the compound of formula (1) from a suitable protic and aprotic solvents or mixture thereof. The step i) may be carried out at a temperature of about 60° C.-140° C., preferably at about 80° C.-120° C.

Step ii) proceeds with complexing the free chelating ligand of formula (1) with a calcium ion source in a protic solvent to furnish Calteridol calcium of formula (1b). Optionally, Calteridol calcium of formula (1b) obtained may be purified by carbon treatment, isolated from protic and aprotic solvents or mixture thereof.

The solvents, bases and resins can be selected from any solvents, bases and resins or mixture thereof as mentioned in the beginning of detail description.

The present invention involves in simple purification techniques for purifying the compounds of formula (1), formula (1a) and formula (1b). In addition, the present invention involves fewer number of steps for the preparation of compounds of formula (1), formula (1a) and formula (1b) with desired purity which is advantageous over prior arts.

In another embodiment, the present invention provides substantially pure Calteridol calcium of formula (1b) with purity greater than 99.0% by High performance liquid chromatography (HPLC).

In another aspect, the present invention provides Calteridol calcium of formula (1b) is having Tri acid impurity, DOTA impurity less than 0.5% (w/w) and more preferably less than 0.2% (w/w)

In another aspect, the present invention provides Regio isomer impurity (13) less than 2% (w/w), preferably less than 1.0% (w/w). More specifically, Calteridol calcium of formula (1b) obtained hereby is having regio isomer of formula (13) content less than 0.5% (w/w).

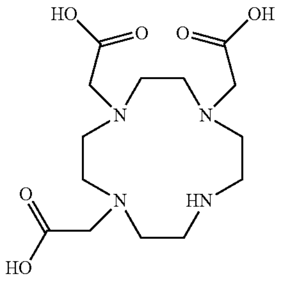

Tri acid Impurity

-continued

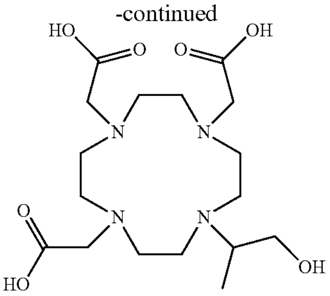

Regio isomer Impurity
(13)

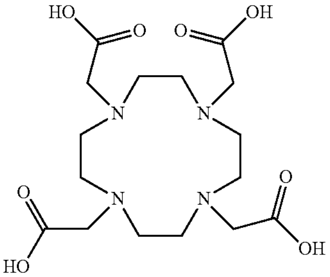

DOTA Impurity

In another embodiment, the present invention provides Calteridol calcium of formula (1b) with water content less than 15% (w/w) by Karl Fischer method.

In another embodiment, the present invention provides Calteridol calcium of formula (1b) with metal content, lead level less than 2 ppm, Arsenic level less than 3 ppm and Iron level less than 5 ppm.

In another embodiment, the present invention provides an amorphous Calteridol calcium of formula (1b).

The present invention is described in the examples given below; further these are provided only to illustrate the invention and therefore should not be construed to limit the scope of the invention.

EXAMPLES

Example-1: Preparation of tert-butyl 2,2',2"-(1,4,7,10-tetraazacyclododecane-1,4,7-triyl) triacetate hydrobromide of Formula (4)

100 g of 1,4,7,10-tetraazacyclododecane of formula (6) was suspended in 500 mL of dimethyl formamide and 250 g of sodium acetate was added at 30-35° C. 395 g of tert-butyl bromoacetate of formula (5) was then added to the reaction mixture. After completion of reaction, water was added and maintained for 1 h. The obtained solid was filtered, washed with water and dried to obtain compound of formula (4). 900 mL toluene was added to compound of formula (4) and 70° C.-75° C. The reaction mixture was cooled to 25° C.-30° C., filtered, washed with toluene and dried to yield pure tert-butyl 2,2',2"-(1,4,7,10-tetraazacyclododecane-1,4,7-triyl) triacetate hydrobromide of formula (4). Yield: 70.0%, Purity by HPLC: 98.0%

Example-2: Preparation of 2,2',2"-(1,4,7,10-tetraazacyclododecane-1,4,7-triyl) triacetic acid of Formula (3)

100 g of tert-butyl 2,2',2"-(1,4,7,10-tetraazacyclododecane-1,4,7-triyl) triacetate hydrobromide of formula (4) was dissolved in sodium hydroxide solution at 25-30° C. The reaction mixture was heated to 95-100° C. and stirred to get the compound 2,2',2"-(1,4,7,10-tetraazacyclododecane-1,4,7-triyl) triacetic acid of formula (3).

Example-3: Preparation of 2,2',2"-(10-(2-hydroxypropyl)-1,4,7,10-tetraazacyclododecane-1,4,7-triyl) triacetic acid of Formula (1)

The reaction mixture obtained in example-2 was cooled to 45-50° C. 27.89 g of propylene oxide of formula (2) was added to the reaction mixture and stirred for 20 minutes. The water was distilled out from the filtrate and the crude material was isolated from methanol and acetone to yield 2,2',2"-(10-(2-hydroxypropyl)-1,4,7,10-tetraazacyclododecane-1,4,7-triyl) triacetic acid of formula (1). Yield: 88.0%

Example-4a: Preparation of Gadoteridol of Formula (1a)

100 g of 2,2',2"-(10-(2-hydroxypropyl)-1,4,7,10-tetraazacyclo dodecane-1,4,7-triyl) triacetic acid (1) was dissolved in 1000 ml of water and 45 g of Gadolinium oxide was added and reaction mixture was heated to 95° C.-100° C. After 3-4 h reaction mixture was cooled to 25° C.-30° C. and filtered. pH of the filtrate was adjusted to 3.0-4.0 with $225H^+$ acidic resin, filtered the resin and washed with water. The pH of the reaction mixture was adjusted to 7.0-8.0 using 810 $OH^-$ resin, filtered the resin and washed with water. The water was distilled out from the filtrate. 260 mL of methanol was added to the crude and heated the reaction mass to reflux temperature for 1 h. The reaction mixture was cooled to 25° C.-30° C., acetone was added to it and stirred for 30 minutes. The obtained solid was washed the acetone and dried at 45° C.-50° C. to get crude Gadoteridol of formula (1). Yield: 83%; Purity: 98%.

Example-4b: Alternate Process for the Preparation of Gadoteridol of Formula (1a)

100 g of 2,2',2"-(10-(2-hydroxypropyl)-1,4,7,10-tetraazacyclo dodecane-1,4,7-triyl) triacetic acid (1) was dissolved in 1000 ml of water and 45 g of Gadolinium oxide was added and reaction mixture was heated to 95° C.-100° C. On completion of reaction, the reaction mass was cooled to 25° C.-30° C. and filtered through Hyflo and washed with water. The water of the filtrate was removed by distillation and 150 mL of methanol added to the concentrated mass at 50-55° C. The reaction mixture was cooled to 25-30° C., acetone was added and filtered under vacuum. The solid so obtained was washed with acetone and dried under vacuum below 50° C. to yield Gadoteridol of formula (1). Yield: 88%; Purity: 98.5%.

Example-4c: Purification of Gadoteridol of Formula (1a)

The obtained crude material was suspended in water, $225H^+$ acidic resin was added, filtered and washed with water. To the filtrate 810 $OH^-$ resin was added, stirred for 30 minutes and filtered. The filtrate may be treated with activated carbon and filtered through Hyflo and then through 0.2-micron filter. The filtrate so obtained may be distilled off and the concentrated mass was diluted with isopropyl alcohol and heated to 70-75° C. The reaction mixture was cooled to 25° C.-30° C., filtered the reaction mass, washed with isopropyl alcohol and dried at 45° C.-50° C. to get pure Gadoteridol of formula (1). Yield: 69%, Purity: 99.8%; PXRD: FIG. 1.

Example-4d: Alternate Purification of Gadoteridol of Formula (1a)

Gadoteridol of formula (1a) was suspended in water and the pH of the solution maintained at 3.0-4.0 using $225H^+$ acidic resin. The reaction mass filtered and to the filtrate 810 $OH^-$ resin was added to maintain the pH of the solution to 7.0-8.0. The reaction mass was stirred and filtered. The filtrate was then treated with activated carbon and filtered through Hyflo and then through 0.2-micron filter. The filtrate so obtained may be distilled off and the concentrated mass was diluted with isopropyl alcohol and heated to 75-85° C. The reaction mixture was cooled to 25° C.-30° C., filtered the reaction mass, washed with isopropyl alcohol and dried to yield pure Gadoteridol of formula (1). Yield: 69%, Purity: 99.8%; PXRD: FIG. 1.

Example-5: Preparation of 2,2',2"-(10-(2-hydroxypropyl)-1,4,7,10-tetraaza cyclododecane-1,4,7-triyl) triacetic acid (1)

220.2 g of oxalic acid was added to a solution of Gadoteridol of formula (1a), in water at 25° C.-30° C. The reaction temperature was raised to 90° C.-100° C. and the mixture was stirred for 5-6 h. After completion of reaction, the reaction temperature was cooled to 25° C.-30° C. The reaction mass was filtered and washed with water. The obtained filtrate was charged with 7.5 L of 225 $H^+$ resin and stirred. The resin was filtered and washed twice with water. To the obtained resin, aqueous ammonium hydroxide was added and heated to 40° C.-45° C. for 1 h. The resin was filtered and washed twice with water. The pH of the obtained filtrate was maintained at 3-3.5 by adding 225 $H^+$ resin. The resin was filtered and washed twice with water. The obtained aqueous layer was concentrated and washed with methanol at below 55° C. 500 mL of methanol was added to the crude reaction mass and heated to the reflux temperature for 1 h. The reaction mixture was cooled to 25° C.-30° C., filtered the material, washed with methanol and dried at below 50° C. to get the titled compound of formula (1). Yield: 64%; Purity: 99.2%

Example-6: Preparation of Calteridol Calcium of Formula (1b)

To a solution of 40 g of 2,2',2"-(10-(2-hydroxypropyl)-1,4,7,10-tetraazacyclo dodecane-1,4,7-triyl) triacetic acid of formula (1) in water, 10.99 g of calcium hydroxide was added and heated to a temperature of 55-65° C. for 2 h. After completion of reaction, the reaction mixture was cooled to 25° C.-30° C. and filtered through Hyflo. The obtained filtrate was treated with activated carbon, filtered and washed twice with water. Aqueous layer was concentrated and washed with methanol at below 55° C. 160 mL of methanol was added to the crude reaction mass and heated to the reflux temperature for 1 h. The reaction mixture was cooled to 45° C.-50° C., acetone was added and stirred for 0.5 h. The obtained solid was filtered, washed with acetone and dried at below 50° C. to yield Calteridol calcium of formula (1b) as amorphous solid. Yield: 83.4%; Purity: 99.1% (HPLC).

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. A high purity Gadoteridol of formula (1a), (1a)

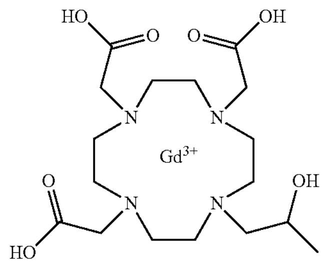

wherein the high purity is characterized by one or more of the following:

a. less than 5 ppm of Iron content;

b. less than 10 ppm of free Gadolinium content and c. less than 0.01% (w/w) of 2,2',2"-(10-(2-hydroxypropyl)-1,4,7,10-tetraazacyclo dodecane-1,4,7-triyl) triacetic acid.

2. A process for the preparation of Gadoteridol of formula (1a) having purity greater than 99.5%

(1a)

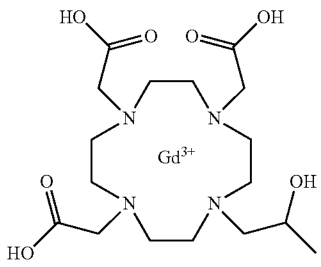

comprising:

a. reacting 1,4,7,10-tetraazacyclododecane of formula (6)

(6)

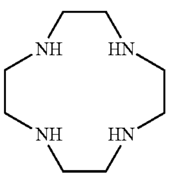

with tert-butyl 2-bromoacetate of formula (5)

(5)

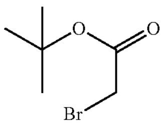

to obtain tert-butyl 2,2',2"-(1,4,7,10-tetraazacyclododecane-1,4,7-triyl) triacetate hydrobromide of formula (4);

(4)

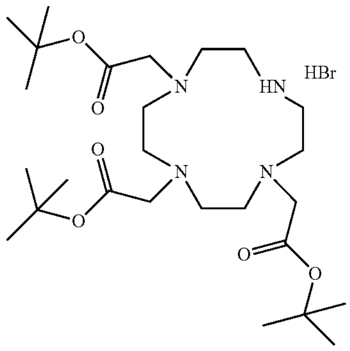

b. hydrolyzing tert-butyl 2,2',2"-(1,4,7,10-tetraazacyclo dodecane-1,4,7-triyl) triacetate hydrobromide of formula (4) to 2,2',2"-(1,4,7,10-tetraazacyclododecane-1,4,7-triyl) triacetic acid of formula (3), optionally isolating intermediate of formula (3);

(3)

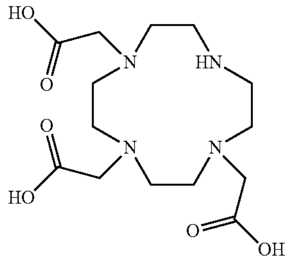

c. alkylating 2,2',2"-(1,4,7,10-tetraazacyclododecane-1,4,7-triyl) triacetic acid compound of formula (3) with propylene oxide of formula (2)

(2)

and treating with a suitable acidic resin furnished chelating ligand 2,2',2"-(10-(2-hydroxypropyl)-1,4,7,10-tetraazacyclo dodecane-1,4,7-triyl) triacetic acid of formula (1); and d. complexing 2,2',2"-(10-(2-hydroxypropyl)-1,4,7,10-tetraazacyclododecane-1,4,7-triyl) triacetic acid of formula (1) with Gadolinium oxide to yield Gadoteridol of formula (1a). Optionally purifying formula (1a), which comprises of;

a) providing a solution of Gadoteridol of formula (1a) in protic solvent or mixture of solvents thereof;

b) treating with a suitable acidic resin;

c) optionally, filtering the reaction mass;

d) treating with a suitable basic resin; and e) isolating pure Gadoteridol of formula (1a).

3. The process as claimed in claim 2, wherein the suitable resin used in the present invention is selected from the group comprising of 225 H+ Acidic resin, Indion 225 Na, Indion 220 Na, Indion 225 H, Indion 225 H (MB), Indion 236, Indion 740, Indion 730, Amberlite IRC 50, Indion 810 $^{-}$OH basic resin or Amberlite IRA 67.

4. The process as claimed in claim 2, wherein Gadoteridol of formula (1a) is having Regio isomer of formula (13) content less than 1% (w/w).

5. A process for the purification of Gadoteridol of formula (1a) comprising;

a. providing a solution of Gadoteridol of formula (1a) in protic solvent or mixture of solvents thereof;

b. adjusting the pH of the solution to 3.0 to 4.0 using suitable acidic resin;

c. optionally, filtering the reaction mass;

d. adjusting the pH of the solution to 7.0-8.0 by adding suitable basic resin; and e. isolating pure Gadoteridol of formula (1a).

6. The process as claimed in claim 5, wherein the suitable protic solvent is selected from the group comprising of methanol, ethanol, isopropanol, propanol, butanol, water or mixtures thereof.

7. A high purity Gadoteridol of formula (1a) is having purity greater than 99.5% and one or more of the following:

a. Less than 0.5% (w/w) of triacid impurity; and b. less than 0.5% (w/w) of 1,4,7,10-tetraazacyclododecane-1,4,7,10-tetraacetic acid.

8. The high purity Gadoteridol of formula (1a) as claimed in claim 1,

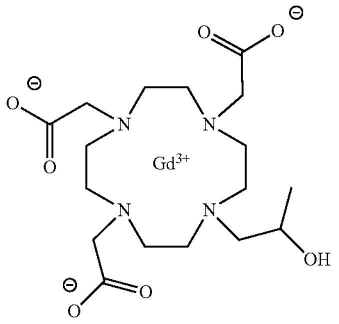

wherein the high purity Gadoteridol of formula (1a) is obtained by an optional purification process comprising the steps of:

a) providing a solution of Gadoteridol of formula (1a) in protic solvent or mixture of solvents thereof;

b) treating with a suitable acidic resin;

c) optionally, filtering the reaction mass;

d) treating with a suitable basic resin; and e) isolating pure Gadoteridol of formula (1a).

9. The high purity Gadoteridol of formula (1a) as claimed in claim 8, wherein the protic solvent is selected from the group consisting of methanol, ethanol, isopropanol, propanol, butanol and water or mixtures thereof.

* * * * *